US010368969B2

(12) United States Patent
Beiersdorf et al.

(10) Patent No.: US 10,368,969 B2
(45) Date of Patent: Aug. 6, 2019

(54) HAND-HELD DEVICE UTILIZING AN ACTIVATION MECHANISM WHICH SPANS THE CIRCUMFERENCE OF SAID DEVICE

(71) Applicants: Rieck A. Beiersdorf, Howards Grove, WI (US); Tammy J. Balzar, Oshkosh, WI (US); Jennifer A. Jensen, Oshkosh, WI (US)

(72) Inventors: Rieck A. Beiersdorf, Howards Grove, WI (US); Tammy J. Balzar, Oshkosh, WI (US); Jennifer A. Jensen, Oshkosh, WI (US)

(73) Assignee: XLR8 Holdings, LLC, Oshkosh, WI (US)

( * ) Notice: Subject to any disclaimer, the term of this patent is extended or adjusted under 35 U.S.C. 154(b) by 204 days.

(21) Appl. No.: 15/493,660

(22) Filed: Apr. 21, 2017

(65) Prior Publication Data
US 2018/0303589 A1    Oct. 25, 2018

(51) Int. Cl.
*A61C 1/00* (2006.01)
*F26B 3/28* (2006.01)
*F26B 9/00* (2006.01)
*A61C 13/15* (2006.01)

(52) U.S. Cl.
CPC .......... *A61C 19/004* (2013.01); *A61C 1/0015* (2013.01); *F26B 3/28* (2013.01); *F26B 9/003* (2013.01)

(58) Field of Classification Search
CPC ....... A61C 19/004; A61C 1/0015; F26B 3/28; F26B 9/003

USPC .......................................................... 34/542
See application file for complete search history.

(56) References Cited

U.S. PATENT DOCUMENTS

| | | |
|---|---|---|
| 4,171,572 A | 10/1979 | Nash |
| 4,330,274 A | 5/1982 | Friedman et al. |
| 4,334,863 A | 6/1982 | Magid et al. |
| 4,340,368 A | 6/1982 | Lococo |
| 4,403,957 A | 9/1983 | Mössle et al. |
| 4,477,252 A | 10/1984 | Lieb et al. |

(Continued)

FOREIGN PATENT DOCUMENTS

| | | | | |
|---|---|---|---|---|
| CA | 2754557 A1 | * | 9/2010 | ........... A61C 1/0015 |
| DE | 19702996 C1 | * | 5/1998 | ........... A61C 1/0015 |

(Continued)

*Primary Examiner* — Stephen M Gravini
(74) *Attorney, Agent, or Firm* — Thomas J. Connelly; Northwind IP Law, S.C.

(57) ABSTRACT

A hand-held device is disclosed which includes an elongated body having a first end, a second end, an exterior surface and a circumference. The elongated body has a cavity formed therein, and at least a portion of the exterior surface creates an ergonomically shaped handle. The hand-held device also includes a tool attached to the first end and an activation mechanism which extends completely around the circumference. The activation mechanism has an outer surface which cooperates with the exterior surface of the elongated body, and the activation mechanism is capable of turning the toll on and off. The hand-held device further includes an electrical circuit positioned within the cavity which connects the activation mechanism to the tool. Lastly, the hand-held device includes a power source for providing power to the electrical circuit when the activation mechanism is turned on.

20 Claims, 2 Drawing Sheets

(56) References Cited

U.S. PATENT DOCUMENTS

| | | | |
|---|---|---|---|
| 4,514,169 A | 4/1985 | Strohmaier | |
| 4,619,614 A | 10/1986 | Baba et al. | |
| 4,626,210 A | 12/1986 | Malata et al. | |
| 4,648,838 A | 3/1987 | Schlachter | |
| 4,661,060 A | 4/1987 | Strohmaier | |
| 4,681,540 A | 7/1987 | Landgraf et al. | |
| 4,744,752 A | 5/1988 | Nakayama et al. | |
| 4,840,563 A | 6/1989 | Altendorf | |
| 5,267,857 A | 12/1993 | Sickler | |
| 5,271,087 A | 12/1993 | Schmid | |
| 5,302,123 A | 4/1994 | Bechard | |
| 5,324,197 A | 6/1994 | Shain et al. | |
| 5,639,236 A | 6/1997 | Martin | |
| 5,669,769 A | 9/1997 | Disel | |
| 5,851,112 A | 12/1998 | Daikuzono | |
| 5,873,717 A | 2/1999 | Behringer | |
| 6,302,692 B1 | 10/2001 | Pond et al. | |
| 6,393,718 B1 * | 5/2002 | Harris | A45D 20/12 34/96 |
| 6,545,390 B1 | 4/2003 | Hahn et al. | |
| 6,793,490 B2 | 9/2004 | Bianchetti et al. | |
| 6,907,678 B2 * | 6/2005 | Cruz | A45D 20/12 34/97 |
| 7,267,547 B2 | 9/2007 | Schmid et al. | |
| 8,967,819 B2 * | 3/2015 | Jaeger | A61C 19/004 200/314 |
| 9,179,990 B2 * | 11/2015 | Benz | A61C 1/0046 |
| 9,468,503 B2 | 10/2016 | Muto et al. | |
| 9,635,713 B2 * | 4/2017 | Groves | H05B 3/009 |
| 2017/0000677 A1 * | 1/2017 | Prince | A61G 15/16 |
| 2018/0303589 A1 * | 10/2018 | Beiersdorf | A61C 19/004 |

FOREIGN PATENT DOCUMENTS

| | | | |
|---|---|---|---|
| EP | 2526894 A1 * | 11/2012 | A61C 19/004 |
| EP | 2465466 B1 * | 10/2016 | A61C 1/0046 |
| JP | 5735409 B2 * | 6/2015 | A61C 1/0046 |

* cited by examiner

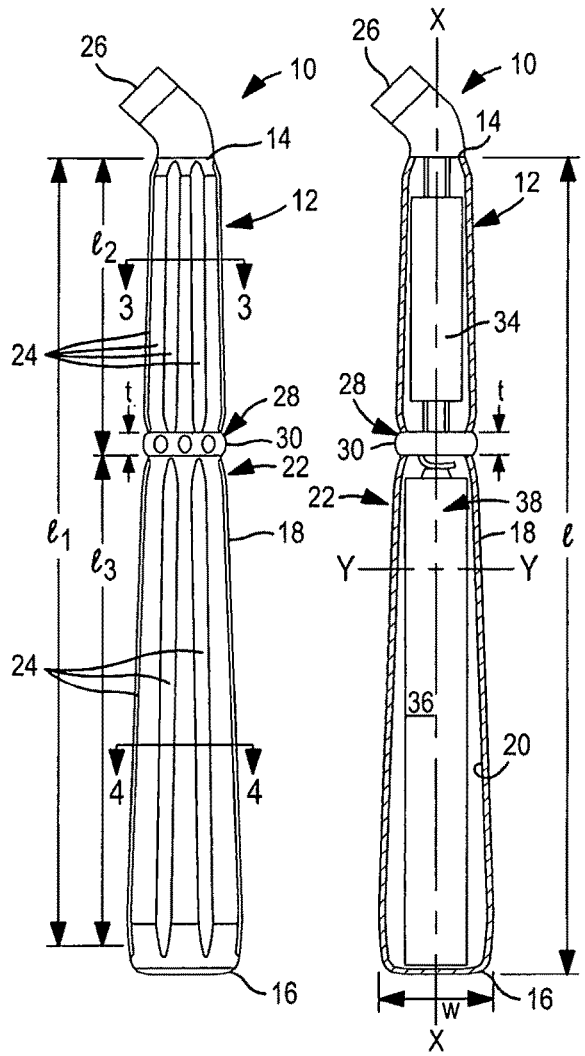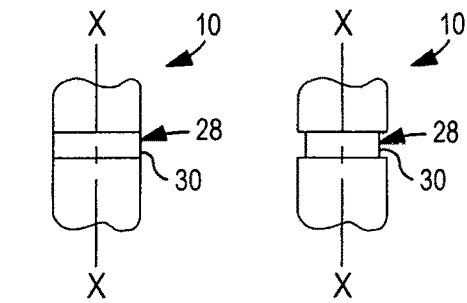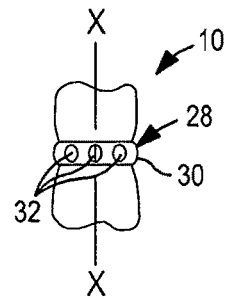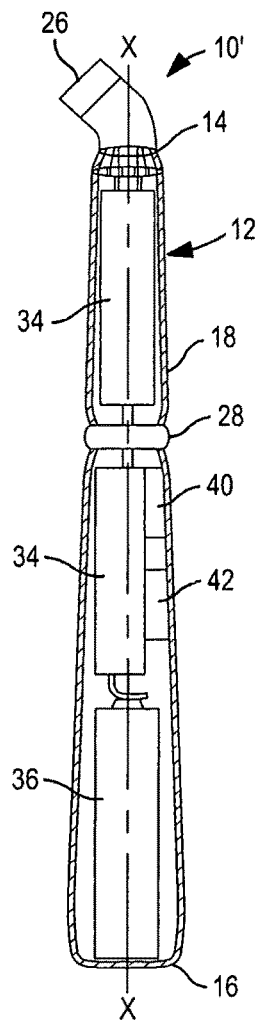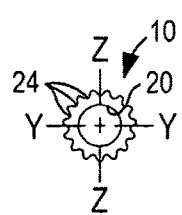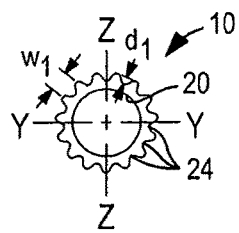

HAND-HELD DEVICE UTILIZING AN ACTIVATION MECHANISM WHICH SPANS THE CIRCUMFERENCE OF SAID DEVICE

FIELD OF THE INVENTION

This invention relates to a hand-held device utilizing an activation mechanism which spans the circumference of the device.

BACKGROUND OF THE INVENTION

Today, various hand-held devices, tools and instruments are used in a variety of settings. Manufacturing employees and construction workers use hand-held devices to create buildings and assemble parts and components; doctors, dentists and other professionals use hand-held tools and instruments to perform various procedures; mechanics use hand-held devices to fix and repair cars, trucks, airplanes, etc.; electricians, carpenters, plumbers, handymen and other craftsmen use hand-held devices and tools to fix and repair a plurality of items. Such hand-held devices come in a variety of sizes and shapes. Some can be used for a number of different tasks, such as a screwdriver, while others are designed to accomplish a single specific task, such as an electric toothbrush or a flashlight.

With the advancement in technology, new hand-held devices, tools and instruments are being developed every day. Today, the medical profession uses light emitting diodes (LEDs) on scopes to probe body cavities and suction devices to remove bodily fluids. Dentists use light emitting diodes to cure or polymerize resin-based composites, as well as various hand-held drills, cleaning instruments, etc. Various other hand-held devices can utilize tungsten halogen lights, plasma arc curing (PAC), lasers, etc. Most of these hand-held devices require an activation mechanism to turn the device on and off. Some of these devices, tools and instruments utilize a light source and/or a motor, which needs to be activated.

The face of many industries and professions is also changing rapidly. Today, more females are serving as doctors, dentist and mechanics. Many work places have seen women take over traditional male jobs. Generally, women tend to be smaller in statute, have smaller hands and may not have the strength of a man. Today's hand-held devices have to accommodate both sexes. In addition, the population in many countries is aging and older workers may be more susceptible to arthritis, carpal tunnel syndrome, etc. Ergonomic stress and fatigue from repetitive motions can affect users of any age. Furthermore, even though most people are right handed, a substantial number of people are left-handed. Today's hand-held devices must accommodate both older workers and right and left handed people.

The activation mechanism needed to turn on and off a particular hand-held device, tool or instrument can vary in size, shape and location. It has been found that a single push button or touch switch, located on the body of a hand-held device is not the most user-friendly feature. This location can cause health issues and be hard to activate.

Now, a hand-held device utilizing an activation mechanism which spans the circumference of the device has been invented which solves the above described problem.

SUMMARY OF THE INVENTION

Briefly, this invention relates to a hand-held device which includes an elongated body having a first end, a second end, an exterior surface and a circumference. The elongated body has a cavity formed therein, and at least a portion of the exterior surface creates an ergonomically shaped handle. A tool is attached to the first end which is capable of performing a function. The tool can be a light emitting diode used to cure a resin based composite. An activation mechanism extends completely around the circumference of the elongated body. The activation mechanism has an outer surface which cooperates with the exterior surface of the elongated body, and the activation mechanism is capable of turning the tool on and off. The hand-held device also includes an electrical circuit positioned within the cavity which connects the activation mechanism to the tool, and a power source for providing power to the electrical circuit when the activation mechanism is turned on.

The invention also relates to a hand-held device which includes an elongated body having a first end, a second end, an exterior surface and a circumference. The elongated body has a cavity formed therein, and at least a portion of the exterior surface creates an ergonomically shaped handle which increases in circumference as the ergonomically shaped handle approaches the second end. A tool is attached to the first end which is capable of performing a function. The tool can be a light emitting diode used to cure a resin-based composite. An activation mechanism extends completely around the circumference of the elongated body. The activation mechanism has an outer surface which is recessed inward from the exterior surface, and the activation mechanism is capable of turning the tool on and off. The hand-held device also includes an electrical circuit positioned within the cavity which connects the activation mechanism to the tool, and a power source for providing power to the electrical circuit when the activation mechanism is turned on.

The invention further relates to a hand-held device which includes an elongated body having a first end, a second end, an exterior surface and a circumference. The elongated body has a cavity formed therein, and at least a portion of the exterior surface creates an ergonomically shaped handle which increases in circumference as the ergonomically shaped handle approaches the second end. A tool is attached to the first end which is capable of performing a function. The tool can be a light emitting diode used to cure a resin based composite. An activation mechanism extends completely around the circumference of the elongated body. The activation mechanism has an outer surface which is aligned flush with the exterior surface, and the activation mechanism is capable of turning the tool on and off. The hand-held device also includes an electrical circuit positioned within the cavity which connects the activation mechanism to the tool, and a power source for providing power to the electrical circuit when the activation mechanism is turned on.

The general object of this invention is to provide a hand-held device which utilizes an activation mechanism which spans the circumference of the device. A more specific object of this invention is to provide a hand-held device which utilizes an activation mechanism in the form of a touch capacitor ring spanning 360 degrees about the circumference.

Another object of this invention is to provide a hand-held device which utilizes an activation mechanism which has an outer surface which extends outward from, is aligned flush with, or is recessed below the exterior surface of the elongated body.

Still another object of this invention is to provide a hand-held device which utilizes an activation mechanism which includes at least two 360° rings which encircle the circumference, and each ring controls a different function of the tool.

A further object of this invention is to provide a hand-held device which utilizes an activation mechanism which is easy to turn on and off.

Still further, an object of this invention is to provide a hand-held device which utilizes an activation mechanism which is inexpensive to manufacture.

Other objects and advantages of the present invention will become more apparent to those skilled in the art in view of the following description and the accompanying drawings.

BRIEF DESCRIPTION OF THE DRAWINGS

FIG. 1 is a schematic of a hand-held device, such as a dental instrument, having a tool attached to a first end, wherein the tool is a light emitting diode used to cure a resin based composite.

FIG. 2 is a vertical cross-sectional view of the hand-held device shown in FIG. 1.

FIG. 3 is a cross-sectional view of the hand-held device shown in FIG. 1 taken along line 3-3.

FIG. 4 is a cross-sectional view of the hand-held device shown in FIG. 1 taken along line 4-4.

FIG. 5 is a partial view of a hand-held device showing an activation mechanism having an outer surface which is aligned flush with the exterior surface of the hand-held device.

FIG. 6 is a partial view of a hand-held device showing an activation mechanism having an outer surface which is recessed inward from the exterior surface of the hand-held device.

FIG. 7 is a partial view of a hand-held device showing an activation mechanism in the form of a 360° ring which includes a number of concentric buttons.

FIG. 8 is a vertical cross-sectional view of a second embodiment of a hand-held device having an activation mechanism which includes a 360° ring in combination with a pair of push buttons which establishes a T-shaped configuration.

DETAILED DESCRIPTION OF THE INVENTION

Figure 9:
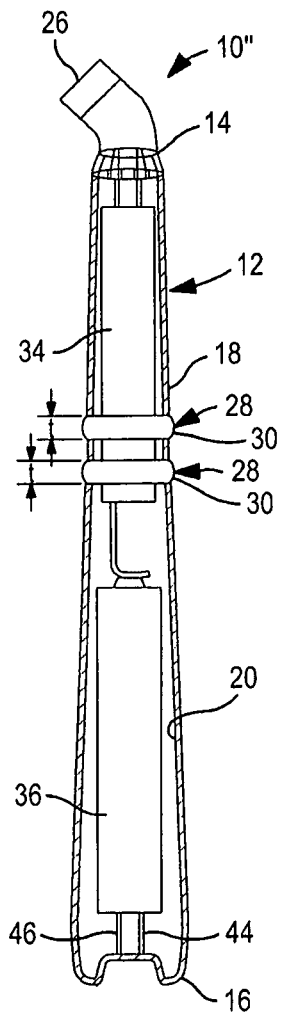
FIG. 9 is a vertical cross-sectional view of a third embodiment of a hand-held device having a pair of activation mechanisms in the form of two 360° rings, and the power source is a rechargeable battery.

Referring to FIGS. 1-4, a hand-held device 10 is shown. The hand-held device 10 can be any device, tool or instrument that can be used by a person to complete a particular task or function. The hand-held device 10 can be a screwdriver, a flashlight, a probe, a medical device, such as a suction instrument, a dental device used to cure a resin based composite, etc. The hand-held device 10 can vary in size, shape, weight, design, function, etc. The hand-held device 10 is a 3-dimensional object having a longitudinal central axis X-X, a vertical central axis Y-Y, and a transverse central axis Z-Z, see FIGS. 3 and 4. Typically, the hand-held device 10 has a length ranging from between about 6 inches to about 10 inches, a width w ranging from about 0.25 inches to about 2 inches, and a weight ranging from a few ounces to a pound. The hand-held device 10 can vary in cross-sectional shape. For example, the hand-held device 10 could have a round, oval, triangular, square, rectangular, pentagon, hexagonal, conical, or some other geometrical shape known to those skilled in the art. By "conical" it is meant having the shape of a cone. In addition, the cross-sectional shape of the hand-held device 10 could vary along its length. Desirably, the hand-held device 10 is ergonomically sculptured to make it easy to grasp and use.

The hand-held device 10 has an elongated body 12 having a first end 14, a second end 16, an exterior surface 18 and a circumference. By "circumference" it is meant the boundary line of a circle, figure, area or object.

The elongated body 12 has a cavity 20 formed therein, see FIGS. 2-4. The cavity 20 can vary in size, shape, volume, etc. For example, the cavity 20 depicted in FIG. 2 extends from the first end 14 to the second end 16 and occupies a substantial portion of the interior of the hand-held device 10. The cavity 20 creates a hollow area in the hand-held device 10.

Referring again to FIG. 1, at least a portion of the exterior surface 18 can be configured to create an ergonomically shaped handle 22. By "ergonomics" it is meant the applied science of equipment design intended to maximize productivity by reducing operator fatigue and discomfort. The handle 22 can include the entire exterior surface 18 situated between the first end 14 and the second end 16 or it can include only a portion of the exterior surface 18. The exterior surface 18 can be configured to fit comfortably into a human hand. Although the hand-held device 10 is depicted as an essentially linear device, it could have an arcuate, sculptured or non-linear shape. The hand-held device 10 can be constructed to fit comfortably into a person's right hand or left hand.

The exterior surface 18 can be formed from a variety of materials. Desirably, the exterior surface 18 is formed from a non-slip material. For example, the exterior surface 18 can be formed from a relatively soft and/or possibly deformable material, such as rubber or plastic. Rubber is a yellowish, amorphous elastic material obtained from the milky sap or latex of various tropical plants, especially the rubber tree, and vulcanized and modified into products. Rubber can also be formed from numerous synthetic elastic materials of varying composition with properties similar to those of natural rubber. Alternatively, the exterior surface 18 can be formed from other materials, including but not limited to: metal, metal composites, plastic, thermoplastic, leather, wood, resin, a composite material, etc. Additionally, the exterior surface 18 could be treated, painted, dipped or coated to obtain a non-slip surface. For example, a rubberized material could be coated onto at least a portion of the exterior surface 18.

The exterior surface 18 could also be shaped, formed, knurled, scored, or be treated so as to acquire a unique configuration which is easy to grasp and which will limit and/or reduce the likelihood that the hand-held device 10 will slip out of a person's hand. By "knurl" it is meant one of a series of small ridges or grooves formed on the surface or edge of an object to aid in gripping.

Furthermore, various kinds of ergonomic grip materials can be applied or secured to the hand-held device 10. Such ergonomic grip materials can include plastic hand grips, rubber hand grips, or foam hand grips. For example, the hand grip could be a sleeve assembly which is removable.

Referring again to FIGS. 1, 3 and 4, the hand-held device 10 is shown with a plurality of longitudinal grooves 24 formed therein. The plurality of longitudinal grooves 24 can form a scallop pattern around the circumference of the hand-held device 10, see FIGS. 3 and 4. The number of grooves 24 can vary, as well as their length, width, depth, configuration, etc. Typically, the number of grooves 24 will depend on the size of the circumference of the hand-held device 10 and their overall configuration. Commonly, from about 8 to about 24 longitudinal grooves 24 can be positioned about the circumference of the hand-held device 10 when the hand-held device 10 has a circumference ranging from between about 0.5 inches to about 2 inches. Desirably, from about 10 to about 20 longitudinal grooves 24 are positioned about the circumference of the hand-held device 10. More desirably, from about 12 to about 18 longitudinal grooves 24 are positioned about the circumference of the hand-held device 10.

Referring again to FIG. 1, each of the plurality of longitudinal grooves 24 has a length $l_1$ which can vary. For example, each of the plurality of longitudinal grooves 24 can have a length $l_1$ which extends from the first end 14 to the second end 16. Alternatively, each of the plurality of longitudinal grooves 24 can have a length which extends over only a portion of the length l of the hand-held device 10. It is also possible to design and configure each of the plurality of longitudinal grooves 24 such that each is not continuous but instead contains a break somewhere along its length $l_1$. In FIG. 1, each of the plurality of longitudinal grooves 24 contains a length consisting of $l_2$ and $l_3$, separated by a break.

Referring to FIG. 4, the width $w_1$ of each of the plurality of longitudinal grooves 24 can also vary. For example, the width $w_1$ of each of the plurality of longitudinal grooves 24 can range from between about 0.01 inches to about 0.25 inches. Desirably, the width $w_1$ of each of the plurality of longitudinal grooves 24 can range from between about 0.02 inches to about 0.13 inches. More desirably, the width $w_1$ of each of the plurality of longitudinal grooves 24 can range from between about 0.025 inches to about 0.12 inches.

Still referring to FIG. 4, the depth $d_1$ of each of the plurality of longitudinal grooves 24 can also vary. For example, the depth $d_1$ of each of the plurality of longitudinal grooves 24 can range from between about 0.01 inches to about 0.15 inches. Desirably, the depth $d_1$ of each of the plurality of longitudinal grooves 24 can range from between about 0.02 inches to about 0.12 inches. More desirably, the depth $d_1$ of each of the plurality of longitudinal grooves 24 can range from between about 0.03 inches to about 0.1 inches. Furthermore, each of the plurality of longitudinal grooves 24 can vary in depth $d_1$ along its length. For example, a longitudinal groove 24 can have a maximum depth $d_1$ located approximate the first end 14, and then taper to a minimum depth $d_1$ located approximate the second end 16, or vice versa. The taper could be continuous or non-continuous. Alternatively, each of the plurality of longitudinal grooves 24 can have a constant depth $d_1$ along its entire length.

In addition to the length $l_1$, the width $w_1$ and the depth $d_1$, of each of the plurality of longitudinal grooves 24 varying, the shape of each of the plurality of longitudinal grooves 24 can also vary. For example, each of the plurality of longitudinal grooves 24 can have a semi-circular configuration, an arcuate configuration, a square configuration or some other geometrical configuration known to those skilled in the art. A concave or scallop configuration works well. By "concave" it is meant curved like the inner surface of a sphere. By "scallop" it is meant one of a series of curved projections forming an ornamental border.

The spacing between each of the plurality of longitudinal grooves 24 can also vary. For example, each of the plurality of longitudinal grooves 24 can abut one another or be offset from one another. When the plurality of longitudinal grooves 24 are offset from one another, the distance between two adjoining longitudinal grooves 24 should be less than 0.13 inches. Desirably, when the plurality of longitudinal grooves 24 are offset from one another, the distance between two adjoining longitudinal grooves 24 should be less than 0.1 inches. More desirably, when the plurality of longitudinal grooves 24 are offset from one another, the distance between two adjoining longitudinal grooves 24 should be less than 0.05 inches.

Each of the plurality of longitudinal grooves 24 function to facilitate gripping and/or cleaning of the hand-held device 10. It is very advantageous when the person using the hand-held device 10 can feel secure that as they grip the hand-held device 10 it will remain positioned in their hand. In addition, especially in the medical and dental fields, it is customary to clean and/or sterilize each hand-held device 10 after each use. When the plurality of longitudinal grooves 24 are aligned parallel to the longitudinal central axis X-X of the hand-held device 10, a person using a cleansing cloth can easily wipe down the hand-held device 10 from the first end 14 to the second end 16 with a disinfectant cloth. By a "disinfectant" it is meant an agent that disinfects by destroying, neutralizing or inhibiting the growth of disease-carrying microorganisms.

It should be understood that the plurality of longitudinal grooves 24 can be aligned parallel to or at an angle to the longitudinal central axis X-X, if desired. An angle of from between about 0° to about 15° works well.

Referring again to FIGS. 1 and 2, the hand-held device 10 has a tool 26 attached or secured to the first end 14. The tool 26 can be any tool or device known to those skilled in the art. The tool 26 can vary in size, shape, type, design, function, etc. For example, the tool 26 can be a light, which can be turned on and off. Examples of lights include: a flashlight, a light bulb, a light emitting diode (LED), an ultraviolet light emitting diode, etc. Various kinds of lights are used in the dental profession to cure resin-based composites. A curing light can be used to set filling material used in repairing cavities. By "curing light" it is meant of or relating to the range of visible radiation wavelengths from about 460 to about 490 nanometers.

The tool 26 could also be a conventional tool such as a drill bit, a screwdriver, a drill, a toothbrush, a rotating brush, a cleaning tool, a probe, etc. The tool 26 can be attached or secure such that it can move, rotate, vibrate, reciprocate, heat up, cool down, turn on a light, etc. The exact mechanism needed to move, rotate, vibrate, reciprocate, heat up, cool down, turn on a light, etc. is not depicted in FIG. 1 or 2 since such mechanisms are well known to those skilled in the art. Furthermore, the tool 26 could include a bendable portion, such as an adjustable neck or head. The bendable portion could be similar to a snake light. The bendable portion could move or rotate up to 360 degrees or more. The bendable portion could also vary in length, similar to a snake light.

The tool 26 can be permanently attached to or be removably secured to the first end 14. For example, it some situations, the person using the hand-held device 10 may want or need to change the size or kind of tool 26. In this case, the tool 26 should be easily removed from the hand-held device 10 and a different tool 26 could be attached to the hand-held device 10.

The tool 26 can be coaxially aligned with the longitudinal central axis X-X of the hand-held device 10 or be aligned at an angle to the longitudinal central axis X-X, as is depicted in FIGS. 1 and 2. The tool 26 can be aligned at an angle ranging from between about 0° to about 90° from the longitudinal central axis X-X. Desirably, the tool 26 can be aligned at an angle ranging from between about 0° to about 60° from the longitudinal central axis X-X. More desirably, the tool 26 can be aligned at an angle ranging from between about 0° to about 45° from the longitudinal central axis X-X. Even more desirably, the tool 26 can be aligned at an angle ranging from between about 0° to about 30° from the longitudinal central axis X-X. Most desirably, the tool 26 can be aligned at an angle ranging from between about 0° to about 20° from the longitudinal central axis X-X.

It is also possible to mount the tool 26 on a quick connector (not shown) such that the tool 26 can be changed with another tool 26 very quickly and easily. Likewise, the tool 26 can be mounted on an adjustable connector (not shown) such that it can be made to move, rotate, vibrate or reciprocate about a set point, path or arc, if desired. Various connectors are well known to those skilled in the art.

The length, width, thickness, and the material from which the tool 26 is constructed can all vary.

Referring again to FIGS. 1 and 2, the hand-held device 10 also includes an activation mechanism 28. By an "activation mechanism" it is meant something that can be used to break or open an electric circuit or divert an electric current from one conductor to another. The activation mechanism 28 extends 360 degrees around the circumference of the hand-held device 10. Desirably, the activation mechanism 28 is one or more 360° rings, each of which extends completely around the circumference of the hand-held device 10. The activation mechanism 28 has an outer surface 30 which cooperates with the exterior surface 18 of the elongated body 12. The function of the activation mechanism 28 is to perform a single function or, alternatively two or more functions. For example, the activation mechanism 28 could be programmed and constructed to turn the tool 26 on and off; control the rate per minute of rotation; control the light intensity; control the duration of time that the light is on; and control the angle of the bendable portion of the tool.

The activation mechanism 28 could also be constructed to emit an audible sound. For example, the activation mechanism 28 could produce an audible sound or emit a noise when it is turned on to alert the operator that the hand-held device is operating. The audible sound could vary in intensity, type of noise, pitch, decibel, etc. For example, the audible sound could be a ringing sound, a chime, a humming sound, a running motor sound, a clicking sound, etc. As shown in FIGS. 1 and 2, the hand-held device 10 has a vertical central axis Y-Y located midway between the first and second ends, 14 and 16 respectively. The activation mechanism 28 is located between the first end 14 and the vertical central axis Y-Y. Desirably, the activation mechanism 28 is located forward of the vertical central axis Y-Y by a distance of up to about 2 inches when the hand-held device 10 has an overall length of about 10 inches or less. Desirably, the activation mechanism 28 is located forward of the vertical central axis Y-Y by a distance of up to about 1.5 inches when the hand-held device 10 has an overall length of about 10 inches or less. More desirably, the activation mechanism 28 is located forward of the vertical central axis Y-Y by a distance of up to about 1 inch when the hand-held device 10 has an overall length of about 10 inches or less.

The activation device 28 is unique in that it provides 360 degrees of touch point activation. This means that the tool 26 can be turned on or off by simply touching the activation mechanism 28 anywhere on its periphery. This construction is advantageous for it means that however a person is holding the hand-held device 10, that person can turn the tool 26 on and off by contacting the activation device 28 with a portion of his or her thumb, finger or some other portion of their hand. The activation mechanism 28 also allows a right-handed person or a left-handed person to easily turn the tool 26 on or off.

Still referring to FIGS. 1 and 2, the activation device 28 has an activation zone thickness t aligned parallel to the longitudinal central axis X-X. The activation zone thickness t can range from between about 0.05 inches to about 0.5 inch. Desirably, the activation zone thickness t ranges from between about 0.1 inches to about 0.3 inches. More desirably, the activation zone thickness t ranges from between about 0.1 inches to about 0.25 inches. Even more desirably, the activation zone thickness t ranges from between about 0.1 inches to about 0.2 inches. Most desirably, the activation zone thickness t is less than about 0.15 inches. The activation zone thickness t should be of a sufficiently size to enable a portion of a person's thumb or finger to easily contact and depress the activation mechanism 28.

The amount of pressure needed to activate the activation mechanism 28 can vary. Generally, a slight amount of pressure is sufficient to activate the activation mechanism 28. The amount of pressure needed to activate the activation mechanism 28 can range from between about 0.01 pounds to about 3 pounds. Desirably, the amount of pressure needed to activate the activation mechanism 28 can range from between about 0.1 pounds to about 1.5 pounds. More desirably, the amount of pressure needed to activate the activation mechanism 28 can range from between about 0.15 pounds to about 1 pound. Even more desirably, the amount of pressure needed to activate the activation mechanism 28 can range from between about 0.2 pounds to about 0.9 pounds. Most desirably, the amount of pressure needed to activate the activation mechanism 28 is less than about 0.5 pounds.

The actual distance that the activation mechanism 28 has to move (be depressed) in order to activate the activation mechanism 28 can vary. Generally, the activation device 28 may have to be depressed a distance of at least about 1 millimeter in order to activate the activation mechanism 28. A millimeter is a unit of length equal to one thousandth ($10^{-3}$) of a meter, or 0.0394 inches. Desirably, the distance the activation device 28 has to move in order to activate the activation mechanism 28 ranges from between about 1 millimeter to about 15 millimeters. More desirably, the distance the activation device 28 has to move in order to activate the activation mechanism 28 ranges from between about 1.5 millimeters to about 10 millimeters. Even more desirably, the distance the activation mechanism 28 has to move in order to activate the activation mechanism 28 ranges from between about 2 millimeters to about 8 millimeters. Most desirably, the distance the activation mechanism 28 has to move in order to activate the activation mechanism 28 is less than about 7 millimeters.

The activation device 28 can vary in size, shape, structure, etc. Desirably, the activation mechanism 28 is a touch point activation mechanism. The activation mechanism 28 could utilize the principals of a push button switch, a toggle switch, a rocker switch, a Piezo switch, a snap action micro switch, a push wheel switch, a side switch, a DIP switch, a thumb reel rotary code switch, a snap action switch, a tactile switch, etc. A DIP switch is a "dual in-line package" switch which utilizes a set of manual electrical switches designed to hold configurations and select the interrupt request (IRQ). The activation mechanism 28 could be a thumb wheel rotary code switch. At least one kind of thumb wheel rotary code switch is commercially available from APEM, having a sales office at 3621 W. Devon Avenue, Chicago, Ill. 60659.

Referring now to FIGS. 1, 5 and 6, the activation mechanism 28 can be a touch capacitor ring which spans 360° about the circumference of the hand-held device 10. The outer surface 30 of the activation mechanism 28 can be raised such that it extends outward from the exterior surface 18 of the hand-held device 10, see FIG. 1. Alternatively, the outer surface 30 of the activation mechanism 28 can be aligned flush with the exterior surface 18 of the hand-held device 10, see FIG. 5. In yet another embodiment, the outer surface 30 of the activation mechanism 28 can be recessed inward from the exterior surface 18 of the hand-held device 10, see FIG. 6. When the outer surface 30 of the activation mechanism 28 extends outward from the exterior surface 18 or is recessed inward from the exterior surface 18, the distance should be relatively small, for example only a few millimeters at the most. Desirably, the distance the outer surface 30 of the activation mechanism 28 extends outward from the exterior surface 18 or is recessed inward from the exterior surface 18 is less than about 10 millimeters. More desirably, the distance the outer surface 30 of the activation mechanism 28 extends outward from the exterior surface 18 or is recessed inward from the exterior surface 18 is less than about 8 millimeters. Even more desirably, the distance the outer surface 30 of the activation mechanism 28 extends outward from the exterior surface 18 or is recessed inward from the exterior surface 18 is less than about 5 millimeters.

The activation mechanism 28 can be a mechanical or an electromechanical switch. The activation device 28 should provide dependability, performance and versatility. The activation mechanism 28 could be illuminated when activated. It may also be advantageous to construct the activation mechanism 28 such that it is waterproof. This feature will facilitate washing and cleaning of the hand-held device 10.

Some manufacturers of the activation mechanism 28, include: Allied Controls (www.alliedcontrols.com/pilot.htm); APEM (www.apem.com); Arcolectric (www.arcolectric.com); Bulgin (www.bulgin.co.uk); Carling Tech (www.carlingtech.com); Cherry (www.cherrycorp.com); CIT Relay & Switch (www.citrelay.com); Copal Electronics (www.copal-electronics.com); Cole-Hersee (www.cole-hersee.com); Coto (www.cotorelay.com); Crouzet (www.crouzet.com); CW Industries (www.cwind.com); Duraswitch (www.duraswitch.com); EAO Switch (www.eaoswitch.com); Eastprint (www.wastprint.com); Electro-Mech Components (www.electromechcomp.com); Electroswitch (www.electroswitch.com); Elma (www.elma.com); Esterline (www.esterline.com); E-Switch (www.e-switch.com); Flex-Core (www.flex-core.com); GC Electronics (www.gcelectronics.com); Grayhill (www.grayhill.com); Hasco (www.hascorelays.com); Haydon Kerk (www.haydonkerk.com); Interpower (www.interpower.com); ITW Switches (www.itwswitches.com); Honeywell Sensing and Control (http://sensing.honeywell.com); Judco manufacturing (www.judco.net); Marquardt Switches (www.switches.com); Meder Electronic (www.meder.com); Memtronik Innovations (www.memtronik.com); Molex (www.molex.com); mec switches (www.mec.dk); NKK Switches (www.nkkswitches.com); Omron (www.omron.com); Otto (www.ottoexcellence.com); Panasonic (www.panasonic.com); Rockwell Automation (www.rockwellautomation.com); Schurter (www.schurter.com); Shogyo (www.shogyo.com); Shokai far East (www.shokifareast.com); Sensata Technologies (www.sensata.com); Sorenson Lighted Controls (www.solico.com); Stacosystems (www.stacosystems.com); Switchcraft (www.switchcraft.com); Switches Unlimited (www.switchesunlimited.com); Tyco Electronics (www.te.com); Ventronics (www.ventronicsinc.com); Wasp Switching Products (www.wasp-switches.co.uk).

Referring now to FIG. 7, the activation mechanism 28 could be constructed as a 360° ring having a concentric number of buttons 32 which are positioned around the circumference of the hand-held device 10. The buttons 32 can be arranged in a series. By "series" it is meant a number of objects arranged or coming after the other in succession. The number of buttons 32 can vary. Desirably, the number of buttons 32 is greater than 6. More desirably, the number of buttons 32 ranges from between about 8 to about 24. More desirably, the number of buttons 32 ranges from between about 10 to about 20. The buttons 32 can also be arranged about the circumference such that they contact one another or are spaced apart from one another. Desirably, the buttons 32 are positioned adjacent to one another but do not touch one another. More desirably, the buttons 32 are space apart from one another from between about 1 millimeter to about 10 millimeters. Even more desirably, the buttons 32 are space apart from one another from between about 1 millimeter to about 5 millimeters. Alternatively, the buttons 32 can be arranged such that they do touch an adjacent button 32.

The buttons 32 are depicted as being circular but could be of some other geometrical shape. For example, the buttons 32 could be oval, square, rectangular, hexagonal, etc. The activation mechanism 28 may be haptic, auditory and/or visual responsive. By "haptic" it is meant of or relating to the sense of touch; tactile. By "auditory" it is meant of or relating to hearing or the sense of hearing. By "visual" it is meant of or relating to the sense of sight; seen or able to be seen by the eye.

The plurality of buttons 32 can be aligned flush with the outer surface 30 of the activation mechanism 28. Alternatively, the plurality of buttons could extend outward from the outer surface 30 of the activation mechanism 28 or be recessed inward from the outer surface 30 of the activation mechanism 28. Furthermore, individual buttons 32 can be designated for certain functions, such as light initiation, light disengagement, light dwell time, light intensity level, etc., if desired.

Returning to FIG. 2, the hand-held device 10 further includes an electrical circuit 34 positioned within at least a portion of the cavity 20. The electrical circuit 34 connects the tool 26 to the activation mechanism 28. When the activation mechanism 28 is activated, the tool 26 will move, rotate, vibrate, reciprocate, light up, etc. The electrical circuit 34 will contain all the elements needed to power the tool 26. Electrical circuits are well known to those skilled in the electrical art.

Lastly, the hand-held device 10 includes a power source 36 for providing power to the electrical circuit 34 when the activation mechanism 28 is turned on. The power source 36 can be one or more batteries, one or more rechargeable batteries, a plug in electrical cord which routes an electrical current from an alternating current outlet to the electrical circuit 34 of the hand-held device 10, a solar panel connected to the hand-held device 10, a combination battery and a plug in electrical cord, etc. By "alternating current" it is meant an electric current which reverses direction at regulate intervals.

It should be understood that the hand-held device 10 could contain an end cap (not shown) which could be screwed or somehow secured to the elongated body 12. The end cap would provide a convenient way to change out the power source (battery) 36. Such end caps are well known to those skilled in the art.

In FIG. 2, the power source 36 is depicted as a single battery 38 positioned in the cavity 20. The battery 38 is electrically connected to the electrical circuit 34.

Referring now to FIG. 8, an alternative hand-held device 10' is depicted which includes an activation mechanism 28 combined with two switches 40 and 42. This arrangement creates a T-shaped configuration. The activation mechanism 28 is a 360° ring, as was described above, which is combined with two vertically arranged switches 40 and 42. The switches 40 and 42 can be depressed to turn them on and off. The switches 40 and 42 do not extend around the circumference of the hand-held device 10' but instead are switches which occupy only a portion of the circumference. In this arrangement, assuming the tool 26 is a light emitting diode used to cure a resin based composite, the activation mechanism 28 can be made to control light initiation or light disengagement, while the two vertically aligned switches 40 and 42 could be used to control light intensity, dwell time, etc. The electrical circuit 34 is sized to accommodate the activation mechanism 28 and the two switches 40 and 42. The power source 36 is depicted as a battery. The battery can be rechargeable. More than one battery could be used, if needed.

It should be understood that the hand-held device 10' could contain an end cap (not shown) which could be screwed or somehow secured to the elongated body 12. The end cap would provide a convenient way to change out the power source (battery) 36. Such end caps are well known to those skilled in the art.

Referring now to FIG. 9, another embodiment of a hand-held device 10" is shown which utilizes a pair of activation mechanisms 28, 28. Each of the pair of activation mechanisms 28, 28 includes a 360° ring which spans the circumference. Each of the pair of activation mechanisms 28, 28 has an outer surface 30. The pair of activation mechanisms 28, 28 are vertically spaced apart and each is aligned along the longitudinal central axis X-X. Each of the pair of activation mechanisms 28, 28 has an activation zone thickness t which can range from between about 0.05 inches to about 0.5 inches. Desirably, the activation zone thickness t ranges from between about 0.1 inches to about 0.3 inches. More desirably, the activation zone thickness t ranges from between about 0.1 inches to about 0.25 inches. Even more desirably, the activation zone thickness t ranges from between about 0.1 inches to about 0.2 inches. Most desirably, the activation zone thickness t is less than about 0.15 inches. The activation zone thickness t should be of a sufficiently size to enable a portion of a person's thumb or finger to easily contact and depress the activation mechanism 28.

Each of the pair of activation mechanisms 28, 28 serves to control a different function of the tool 26. For example, one activation mechanism 28 could turn the tool 26 on and off, while another activation mechanism 28 could control the rate per minute (rpm) of rotation, a third activation mechanism 28 could control the light intensity, and a fourth activation mechanism 28 could control the duration or other variables of the tool 26. Alternatively, each of the pair of activation mechanisms 28, 28 could be designed and constructed to perform a single task or multitask such that it can accomplish two or more of these functions. For example, one of the pair of activation mechanisms 28, 28 could be programmed and constructed to turn the tool 26 on and off; and also control the rate per minute of rotation. The second of the pair of activation mechanisms 28, 28 could be programmed and constructed to control the light intensity and control the duration of time that the light is on.

It should be understood that each of the pair of activation mechanisms 28, 28 could be programmed and constructed to control a single task or two or more functions.

Each of the pair of activation mechanisms 28, 28 could be illuminated when activated. Likewise, the pair of activation mechanisms 28, 28 could be constructed to be waterproof. This feature will facilitate washing and cleaning of the hand-held device 10".

The hand-held device 10" contains a power source 36 in the form of a rechargeable battery. Two prongs 44 and 46 extend from the power source 36 and pass through the second end 16 of the hand-held device 10". The two prongs 44 and 46 are sized and designed to mate with a pair of orifices located in a charger (not shown). When the hand-held device 10" is connected to the charger, the power source 36 an be recharged.

Figure 10:
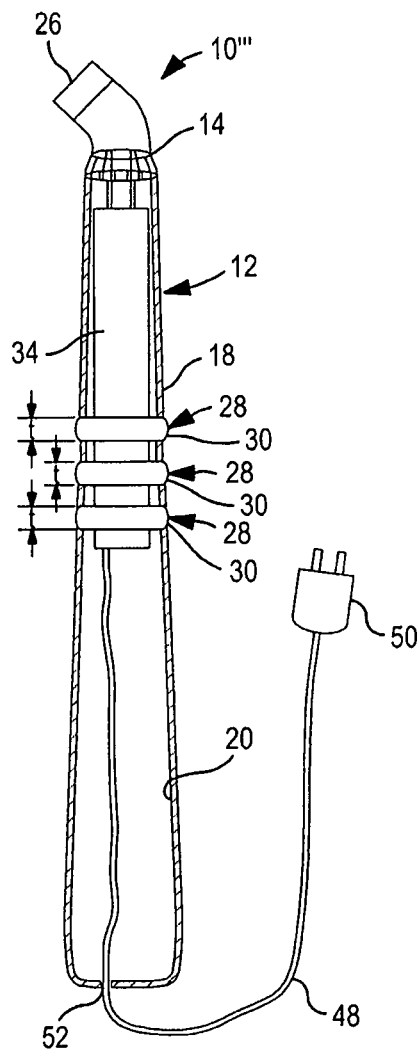
FIG. 10 is a vertical cross-sectional view of a fourth embodiment of a hand-held device having three activation mechanisms in the form of three 360° rings, and the power source is an electrical cord which routes electricity to the hand-held device.

Referring now to FIG. 10, still another embodiment of a hand-held device 10''' is shown which utilizes three activation mechanisms 28, 28 and 28. Each of the three activation mechanisms 28, 28 and 28 includes a 360° ring which spans the circumference.

The three activation mechanisms 28, 28 and 28 are vertically spaced apart from one another and they are aligned along the longitudinal central axis X-X. Each of the three activation mechanisms 28, 28 and 28 has an outer surface 30. Each of the three activation mechanisms 28, 28 and 28 has an activation zone thickness t which can range from between about 0.05 inches to about 0.5 inches. Desirably, the activation zone thickness t ranges from between about 0.1 inches to about 0.3 inches. More desirably, the activation zone thickness t ranges from between about 0.1 inches to about 0.25 inches. Even more desirably, the activation zone thickness t ranges from between about 0.2 inches to about 0.2 inches. Most desirably, the activation zone thickness t is less than about 0.15 inches. The activation zone thickness t should be of a sufficiently size to enable a portion of a person's thumb or finger to easily contact and depress the activation mechanism 28.

Each of the three activation mechanisms 28, 28 and 28 serves to control a different function of the tool 26. For example, one activation mechanism 28 could turn the tool 26 on and off, the second activation mechanism 28 could control the rate per minute (rpm) of rotation of the tool 26, and the third activation mechanism 28 could control the torque provided to the tool 26.

Each of the three activation mechanisms 28, 28 and 28 could be illuminated when activated.

The hand-held device 10''' contains a power source 36 in the form of an electrical cord 48 which contains a plug in adapter 50 secured to its distal end. The electrical cord 48 passes through an aperture 52 formed through the second end 16 of the hand-held device 10'''. The electrical cord 48, which can vary in length, is designed to route an electrical current from an alternating current source, such as an electrical outlet in an office, business, home, etc. to the electrical circuit 34. The electrical circuit 34 is connected to all three activation mechanisms 28, 28 and 28.

As stated above with reference to the hand-held device 10, all three of the activation mechanisms 28, 28 and 28 could be illuminated when activated. Likewise, all three of the activation mechanisms 28, 28 and 28 could be constructed to be waterproof. This feature will facilitate washing and cleaning of the hand-held device 10".

It should be understood that in the embodiments shown in FIGS. 9 and 10, that the outer surface 30 of each of the activation mechanisms 28 can extend outward from the exterior surface 18, be aligned flush with the exterior surface, or be recessed inward from the exterior surface 18, as was explained above with reference to the hand-held device 10. The distance that the outer surface 30 is spaced outward from or is recessed inward from the exterior surface 18 can range from between about 1 millimeter to about 10 millimeters. Lastly, the activation zone thickness t of each activation mechanism 28 can range from between about 0.05 inches to about 0.5 inches.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:
1. A hand-held device comprising:
   a) an elongated body having a first end, a second end, an exterior surface and a circumference, said elongated body having a cavity formed therein, and at least a portion of said exterior surface creates an ergonomically shaped handle;
   b) a tool attached to said first end which is capable of performing a function;
   c) an activation mechanism extending 360 degrees around said circumference, said activation mechanism having an outer surface which cooperates with said exterior surface of said elongated body, and said activation mechanism is capable of performing a function;
   d) an electrical circuit positioned within said cavity which connects said activation mechanism to said tool; and
   e) a power source for providing power to said electrical circuit when said activation mechanism is turned on.

2. The hand-held device of claim 1 wherein said tool includes a bendable portion, further comprises a plurality of from 8 to 24 longitudinal grooves which form a scallop pattern around said circumference, each of said longitudinal grooves having a depth ranging from between 0.01 inches to 0.15 inches, and said plurality of longitudinal grooves facilitating gripping said device.

3. The hand-held device of claim 2 wherein said hand-held device has a vertical central axis located midway between said first and second ends, said activation mechanism is located between said first end and said vertical central axis, and said activation mechanism could be programmed and constructed to control a single function or two or more functions.

4. The hand-held device of claim 3 wherein said activation mechanism is located forward of said vertical central axis by a distance of up to about 1.5 inches, and said activation mechanism is aligned flush with said exterior surface.

5. The hand-held device of claim 2 wherein said device has a longitudinal central axis and each of said plurality of longitudinal grooves is aligned at an angle of from between 0 degrees to about 15 degrees to said longitudinal central axis, said activation mechanism is a touch capacitor ring spanning 360 degrees of said circumference, and said power source is a battery positioned within said cavity.

6. The hand-held device of claim 1 wherein said activation mechanism is a thumb wheel rotary code switch, and said power source is an electrical cord which routes an electrical current from an alternating current outlet to said electrical circuit.

7. The hand-held device of claim 1 wherein said activation mechanism is recessed below said exterior surface a distance of from between about 1 millimeter to about 10 millimeters, and said activation mechanism has an activation zone thickness which ranges from between about 0.05 inches to about 0.5 inches.

8. The hand-held device of claim 1 wherein said activation mechanism includes at least two rings, with each of said at least two rings spanning 360 degrees about said circumference, each of said at least two rings has an activation zone thickness ranging from about 0.05 inches to about 0.5 inches, and each of said at least two rings controlling a different function of said tool.

9. The hand-held device of claim 1 wherein said activation mechanism has an outer surface which is aligned flush with said exterior surface, said activation mechanism is illuminated when turned on, and said activation mechanism can perform a single task or two or more tasks simultaneously.

10. A hand-held device comprising:
   a) an elongated body having a first end, a second end, an exterior surface and a circumference, said elongated body having a cavity formed therein, and at least a portion of said exterior surface creates an ergonomically shaped handle which increases in circumference as said ergonomically shaped handle approaches said second end;
   b) a tool attached to said first end which is capable of performing a function;
   c) an activation mechanism extending 360 degrees around said circumference, said activation mechanism having an outer surface which is raised and extends outward from said exterior surface, and said activation mechanism is capable of performing a function;
   d) an electrical circuit positioned within said cavity which connects said activation mechanism to said tool; and
   e) a power source for providing power to said electrical circuit when said activation mechanism is turned on.

11. The hand-held device of claim 10 wherein said ergonomically shaped handle contains a plurality of from 8 to 24 longitudinal grooves which form a scallop pattern around said circumference, each of said plurality of longitudinal grooves extend from said activation mechanism to said second end, said plurality of longitudinal grooves facilitating gripping and cleaning of said hand-held device, and said tool is a light emitting diode.

12. The hand-held device of claim 10 wherein said ergonomically shaped handle contains a plurality of longitudinal grooves which extend from said first end to said activation mechanism and from said activation mechanism to said second end, said plurality of longitudinal grooves having a maximum depth located approximate said first end, said plurality of longitudinal grooves tapering to a minimum depth located approximate said second end, and said plurality of longitudinal grooves facilitating gripping and cleaning of said hand-held device.

13. The hand-held device of claim 10 wherein said cavity extends from said first end to said second end, said power source includes an electrical cord which can route an electrical current from an alternating current source to said electrical circuit, and said electrical cord passes through an aperture formed through said second end.

14. The hand-held device of claim 10 wherein said activation mechanism can be illuminated when turned on, said activation mechanism is waterproof, and said tool is a light emitting diode which can be used to cure a resin based composite.

15. The hand-held device of claim 10 wherein said activation mechanism is a ring having a concentric series of buttons which span 360 degrees about said circumference.

16. A hand-held device comprising:
   a) an elongated body having a first end, a second end, an exterior surface and a circumference, said elongated body having a cavity formed therein, and at least a portion of said exterior surface creates an ergonomically shaped handle which increases in circumference as said ergonomically shaped handle approaches said second end;
   b) a tool attached to said first end which is capable of performing a function;
   c) an activation mechanism extending 360 degrees around said circumference, said activation mechanism having an outer surface which is aligned flush with said exterior surface, and said activation mechanism is capable of performing a function;
   d) an electrical circuit positioned within said cavity which connects said activation mechanism to said tool; and
   e) a power source for providing power to said electrical circuit when said activation mechanism is turned on.

17. The hand-held device of claim 16 wherein said exterior surface is formed from a non-slip material.

18. The hand-held device of claim 17 wherein said activation mechanism could be programmed and constructed to control at least one function.

19. The hand-held device of claim 16 wherein said activation mechanism is a touch capacitor ring which spans 360 degrees about said circumference, said power source is a rechargeable battery positioned within said cavity, and said tool is a light emitting device.

20. The hand-held device of claim 19 wherein said light emitting device is a light emitting diode which can be used to cure a resin based composite.

* * * * *